(12) United States Patent
Zhao et al.

(10) Patent No.: US 12,727,999 B2
(45) Date of Patent: Sep. 8, 2026

(54) HEART VALVE DELIVERY ASSEMBLY AND UNLOCKING TUBE

(71) Applicant: Lepu Medical Technology (Beijing) Co., Ltd., Beijing (CN)

(72) Inventors: Xuancheng Zhao, Beijing (CN); Kejin Qiu, Beijing (CN); Shuaibing Li, Beijing (CN); Rencao Chang, Beijing (CN)

(73) Assignee: Lepu Medical Technology (Beijing) Co., Ltd., Beijing (CN)

( * ) Notice: Subject to any disclaimer, the term of this patent is extended or adjusted under 35 U.S.C. 154(b) by 0 days.

(21) Appl. No.: 18/991,913

(22) Filed: Dec. 23, 2024

(65) Prior Publication Data

US 2026/0020957 A1 Jan. 22, 2026

Related U.S. Application Data

(63) Continuation of application No. PCT/CN2024/119915, filed on Sep. 20, 2024.

(30) Foreign Application Priority Data

Jul. 16, 2024 (CN) ......................... 202410949797.3

(51) Int. Cl.
*A61F 2/24* (2006.01)
*A61F 2/95* (2013.01)

(52) U.S. Cl.
CPC .......... *A61F 2/2436* (2013.01); *A61F 2/2418* (2013.01); *A61F 2/95* (2013.01); *A61F 2002/9505* (2013.01); *A61F 2002/9511* (2013.01); *A61F 2220/0025* (2013.01);
(Continued)

(58) Field of Classification Search
CPC .. A61F 2/2436–2439; A61F 2002/9505; A61F 2220/0083
See application file for complete search history.

(56) References Cited

U.S. PATENT DOCUMENTS

| | | | |
|---|---|---|---|
| 2017/0231765 A1 | 8/2017 | Desrosiers et al. |
| 2019/0059876 A1 | 2/2019 | Decker et al. |

FOREIGN PATENT DOCUMENTS

| | | |
|---|---|---|
| CN | 111821068 A | 10/2020 |
| CN | 113855330 A | 12/2021 |

(Continued)

*Primary Examiner* — Rebecca S Preston
(74) *Attorney, Agent, or Firm* — George D. Morgan

(57) ABSTRACT

The present disclosure relates to a heart valve delivery assembly and an unlocking tube. An outer tube apparatus is included, and includes an outer tube and a plurality of unlocking structures. Each unlocking structure includes an unlocking tube and a traction strip which are interconnected, where the unlocking tube includes a spring tube and a limiting structure, the limiting structure includes a first tube, a second tube, and a connecting strip, the first tube and the second tube are coaxially arranged, the first tube and the second tube are spaced and are connected through the connecting strip, the spring tube is located in an interval space. When a valve stent is released, it can be ensured that the unlocking tube moves towards a proximal side as a whole, thereby exposing a connection position of a hanging ear and a hanging head, and ensuring successful release of the valve stent.

5 Claims, 10 Drawing Sheets

(52) U.S. Cl.
CPC ................. *A61F 2220/0083* (2013.01); *A61F 2230/0091* (2013.01)

(56) References Cited

FOREIGN PATENT DOCUMENTS

| | | | | | |
|---|---|---|---|---|---|
| CN | 216754724 | U | * | 6/2022 | ............... A61F 2/24 |
| WO | WO2021026184 | A1 | | 2/2021 | |

* cited by examiner

HEART VALVE DELIVERY ASSEMBLY AND UNLOCKING TUBE

CROSS-REFERENCE TO RELATED APPLICATIONS

The application claims priority to Chinese patent application No. 2024109497973, filed on Jul. 16, 2024, the entire contents of which are incorporated herein by reference.

TECHNICAL FIELD

The present disclosure belongs to the technical field of medical instruments, and specifically, to a heart valve delivery assembly and an unlocking tube.

BACKGROUND

The prior art CN113855330A discloses a structure for quickly connecting and releasing a heart valve stent, which discloses a spring-loaded unlocking sleeve capable of axial extension and retraction. When a hanging ear is connected to a hanging head on the valve stent, the unlocking sleeve can be compressed in a proximal direction to expose the hanging ear from a distal end of the unlocking sleeve, thereby facilitating the connection between the hanging head and the hanging ear. After the connection is completed, the unlocking sleeve is released, making the length of the hanging ear increased. The distal end of the unlocking sleeve moves towards one side of the hanging head, such that a head end of the hanging ear and the hanging head enter the unlocking sleeve, thereby preventing the hanging ear from separating from the hanging head. However, when the valve stent needs to be released, the unlocking sleeve is pulled towards the proximal side, but due to the existence of resistance, the proximal end of the unlocking sleeve moves towards the proximal side while the position of the distal end of the unlocking position is basically kept unchanged, so as to lengthen the unlocking sleeve. A connection position of the hanging ear and the hanging head is located in a distal portion of the unlocking sleeve, such that the connection position cannot be exposed, leading to unsuccessful release of the heart valve, and affecting the progress of the interventional surgery.

SUMMARY

In view of this, the present disclosure provides a heart valve delivery assembly and an unlocking tube. When a valve stent is released, it can be ensured that an unlocking tube moves towards a proximal side as a whole, thereby exposing a connection position of a hanging ear and a hanging head, and ensuring successful release of the valve stent.

The technical solution adopted by the present disclosure is as follows:

a heart valve delivery assembly includes an outer sheath, an outer tube apparatus, an inner tube apparatus, and a valve stent.

The outer tube apparatus includes an outer tube and a plurality of unlocking structures; each unlocking structure includes an unlocking tube and a traction strip which are interconnected, where the unlocking tube includes a spring tube and a limiting structure, the limiting structure includes a first tube, a second tube, and a connecting strip, the first tube and the second tube are coaxially arranged, the first tube and the second tube are spaced in an axial direction of the first tube, such that an interval space is formed between the first tube and the second tube, the first tube and the second tube are connected through the connecting strip, the spring tube is located in the interval space, an axis of the spring tube and an axis of the first tube are located on the same straight line, one end of the spring tube is connected to the first tube, an adjustment space is formed between the other end of the spring tube and the second tube, the traction strip is connected to the other end of the spring tube, and the unlocking structure is connected to a distal end of the outer tube through the traction strip; and in a circumferential direction of the outer tube, the plurality of unlocking structures are arranged with equal angles;

- the inner tube apparatus includes an inner tube and a plurality of hanging ears, the number of the hanging ears is equal to the number of the unlocking structures, with each corresponding to one another, the plurality of hanging ears are connected to a distal end of the inner tube, in a circumferential direction of the inner tube, the plurality of hanging ears are arranged with equal angles, the inner tube is located inside the outer tube, and the hanging ears penetrate through the second tubes, the spring tubes, and the first tubes of the unlocking structures;
- the valve stent includes a stent and a valve, the valve is applied to the stent, one end of the stent is provided with a plurality of hanging heads, the number of the hanging heads is equal to the number of the hanging ears, with each corresponding to one another, and correspondingly, the hanging ears are connected to the hanging heads; and
- the outer tube is sleeved with the outer sheath.

Preferably, one end of the first tube close to the second tube is provided with a first connection point, the first connection point is located on a peripheral surface of the first tube, one end of the second tube close to the first tube is provided with a second connection point, the second connection point is located on a peripheral surface of the second tube, in a circumferential direction of the first tube, the first connection point and the second connection point are located at the same position, one end of the connecting strip is connected to the first connection point, and the other end of the connecting strip is connected to the second connection point;

- the connecting strip includes a first inclined segment, a straight segment, and a second inclined segment, which are sequentially connected, and the straight segment is parallel to the axis of the first tube; and
- in a direction from the first tube to the second tube, the first inclined segment inclines towards a radial outer side of the first tube, and the second inclined segment inclines towards a radial inner side of the first tube.

Preferably, the spring tube includes a first tube segment, a spring segment, and a second tube segment, which are sequentially connected, the first tube segment is connected to the first tube, and the traction strip is connected to the second tube segment.

Preferably, an internal diameter of the first tube, an internal diameter of the first tube segment, an internal diameter of the second tube segment, and an internal diameter of the second tube are equal, and an external diameter of the first tube, an external diameter of the first tube segment, an external diameter of the second tube segment, and an external diameter of the second tube are equal; and

- in a natural state, an internal diameter of the spring segment is equal to the internal diameter of the first tube segment, and an external diameter of the spring segment is equal to the external diameter of the first tube segment.

Preferably, in the natural state, the other end of the spring tube abuts against the second tube.

The present disclosure further relates to an unlocking tube. The unlocking tube is the unlocking tube in the above heart valve delivery assembly.

The present disclosure has the beneficial effects:

in the present disclosure, an unlocking sleeve in the prior art is replaced with the unlocking tube, the traction strip has certain rigidity and is connected to the other end (a proximal end) of the spring tube, a distal end of the spring tube is connected to the first tube, the hanging ear penetrates through the spring tube, and in the natural state, a distal end of the hanging ear is located in the first tube; when the heart valve delivery assembly is assembled, the hanging ear needs to be connected to the hanging head on the valve stent, in this case, the first tube is manually pressed to move towards the proximal side, and since the traction strip has certain rigidity, the traction strip pushes the proximal end of the spring tube, the proximal end of the spring tube cannot move towards the proximal side, and as a result, the spring tube is compressed, and the distal end of the hanging ear is exposed from the first tube, thereby facilitating the connection of the hanging ear and the hanging head. After the hanging ear and the hanging head are connected, the first tube is released, the spring tube is not compressed any more and extends under the action of elastic force to cause the first tube to move towards a distal side, thereby allowing the hanging head and the distal end of the hanging ear to enter the first tube and preventing the hanging head from separating from the hanging ear.

When the valve stent needs to be released, the traction strip is pulled towards the proximal side, and the traction strip pulls the proximal end of the spring tube, thereby causing the proximal end of the spring tube to move towards the proximal side. Even if the first tube cannot move towards the proximal side due to resistance, the spring tube is stretched until the proximal end of the spring tube makes contact with the second tube. Since the second tube and the first tube are connected through the rigid connecting strip, the spring tube is continuously pulled towards the proximal side to push the second tube to move towards the proximal side, thereby causing the first tube to move towards the proximal side as well, so as to expose the connection position of the hanging ear and the hanging head, successfully achieve valve release, and ensure smooth proceeding of the interventional surgery.

BRIEF DESCRIPTION OF DRAWINGS

The above and other objectives, features, and advantages of the present disclosure are more apparent through the following description of the embodiments of the present disclosure with reference to the accompanying drawings. In the accompanying drawings.

Figure 1:
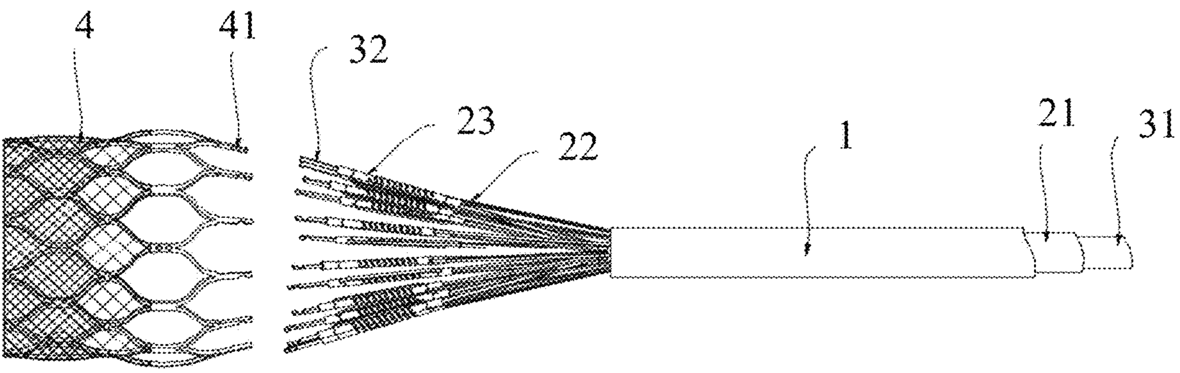
FIG. 1 is a schematic diagram of a structure of a heart valve delivery assembly.
Figure 2:
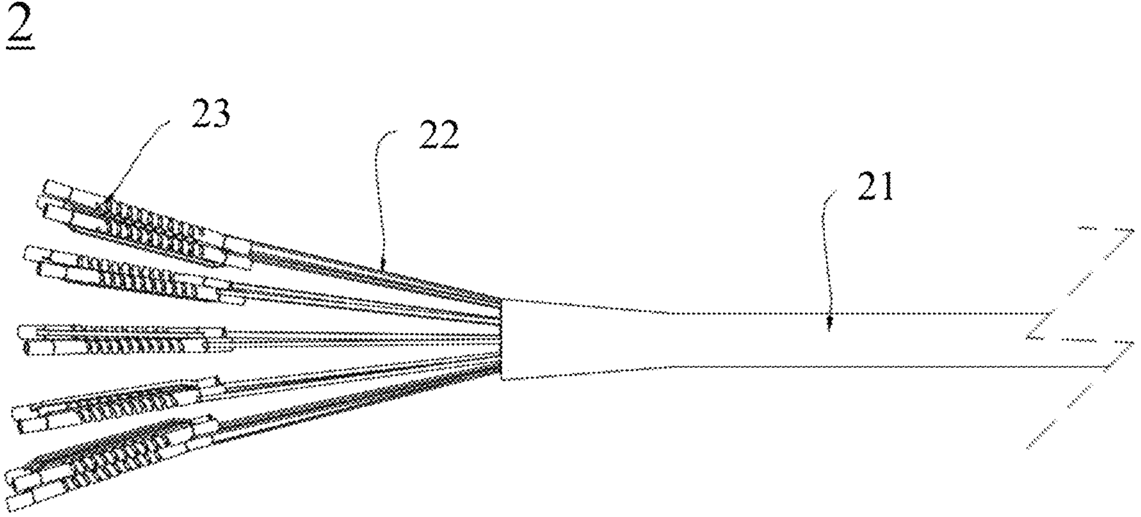
FIG. 2 is a schematic diagram of a structure of an outer tube apparatus.
Figure 3:
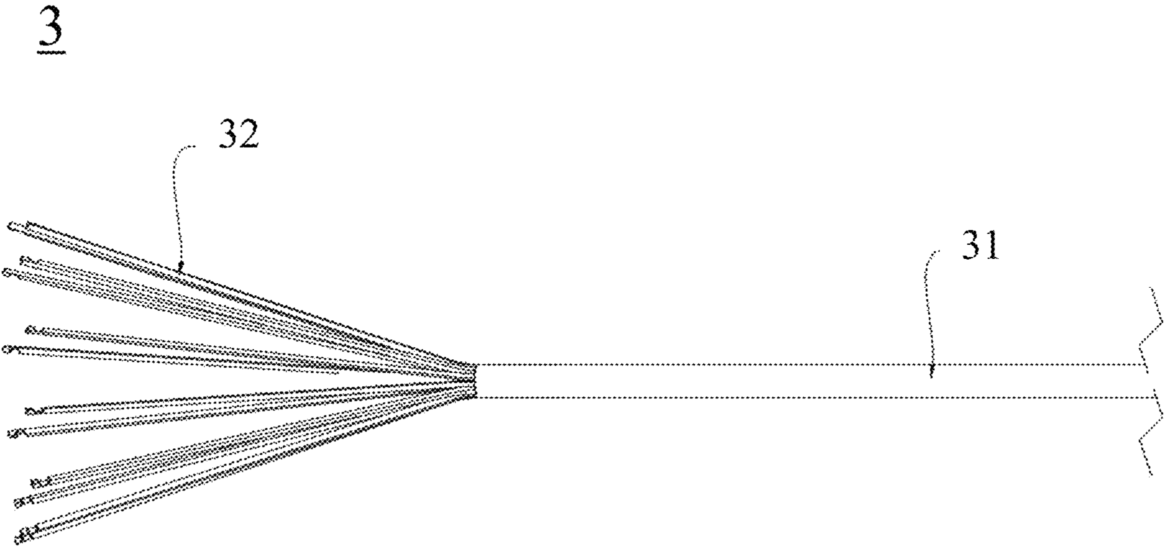
FIG. 3 is a schematic diagram of a structure of an inner tube apparatus.

In the figures: 1—outer sheath; 2—outer tube apparatus; 3—inner tube apparatus; 4—valve stent;

21—outer tube; 22—traction strip; 23—unlocking tube; 24—limiting structure; 25—spring tube; 26—adjustment space;

31—inner tube; 32—hanging ear;

41—hanging head;

241—first tube; 242—second tube; 243—connecting strip;

251—first tube segment; 252—second tube segment; and 253—spring segment.

DETAILED DESCRIPTION OF THE EMBODIMENTS

The present disclosure is described below based on embodiments, but the present disclosure is not merely limited to these embodiments. In the detailed description of the present disclosure below, some specific details are elaborated to avoid obscuring the essence of the present disclosure. Well-known methods, processes, flows, and components are not described in detail.

Referring to FIG. 1 to FIG. 10, the present disclosure provides a heart valve delivery assembly, including an outer sheath 1, an outer tube apparatus 2, an inner tube apparatus 3, and a valve stent 4.

The outer tube apparatus 2 includes an outer tube 21 and a plurality of unlocking structures. Each unlocking structure includes an unlocking tube 23 and a traction strip 22 which are interconnected, where the unlocking tube 23 includes a spring tube 25 and a limiting structure 24, the limiting structure 24 includes a first tube 241, a second tube 242, and a connecting strip 243, the first tube 241 and the second tube 242 are coaxially arranged, and the first tube 241 and the second tube 242 are spaced in an axial direction of the first tube 241, such that an interval space is formed between the first tube 241 and the second tube 242; the first tube 241 and the second tube 242 are connected through the connecting strip 243, the spring tube 25 is located in the interval space, an axis of the spring tube 25 and an axis of the first tube 241 are located on the same straight line, and one end of the spring tube 25 is connected to the first tube 241; and an adjustment space 26 (preferably, the length of the adjustment space 26 is 0) is formed between the other end of the spring tube 25 and the second tube 242, the traction strip 22 is connected to the other end of the spring tube 25, and the unlocking structure is connected to a distal end of the outer tube 21 through the traction strip 22. In a circumferential direction of the outer tube 21, the plurality of unlocking structures are arranged with equal angles.

The inner tube apparatus 3 includes an inner tube 31 and a plurality of hanging ears 32. The number of the hanging ears 32 is equal to the number of the unlocking structures, with each corresponding to one another. The plurality of hanging ears 32 are connected to a distal end of the inner tube 31. In a circumferential direction of the inner tube 31, the plurality of hanging ears 32 are arranged with equal angles, the inner tube 31 is located inside the outer tube 21, and the hanging ears 32 penetrate through the second tubes 242, the spring tubes 25, and the first tubes 241 of the unlocking structures.

The valve stent 4 includes a stent and a valve. The valve is applied to the stent, and one end of the stent is provided with a plurality of hanging heads 41. The number of the hanging heads 41 is equal to the number of the hanging ears 32, with each corresponding to one another, and correspondingly, the hanging ears 32 are connected to the hanging heads 41.

The outer tube 21 is sleeved with the outer sheath 1.

Figure 4:
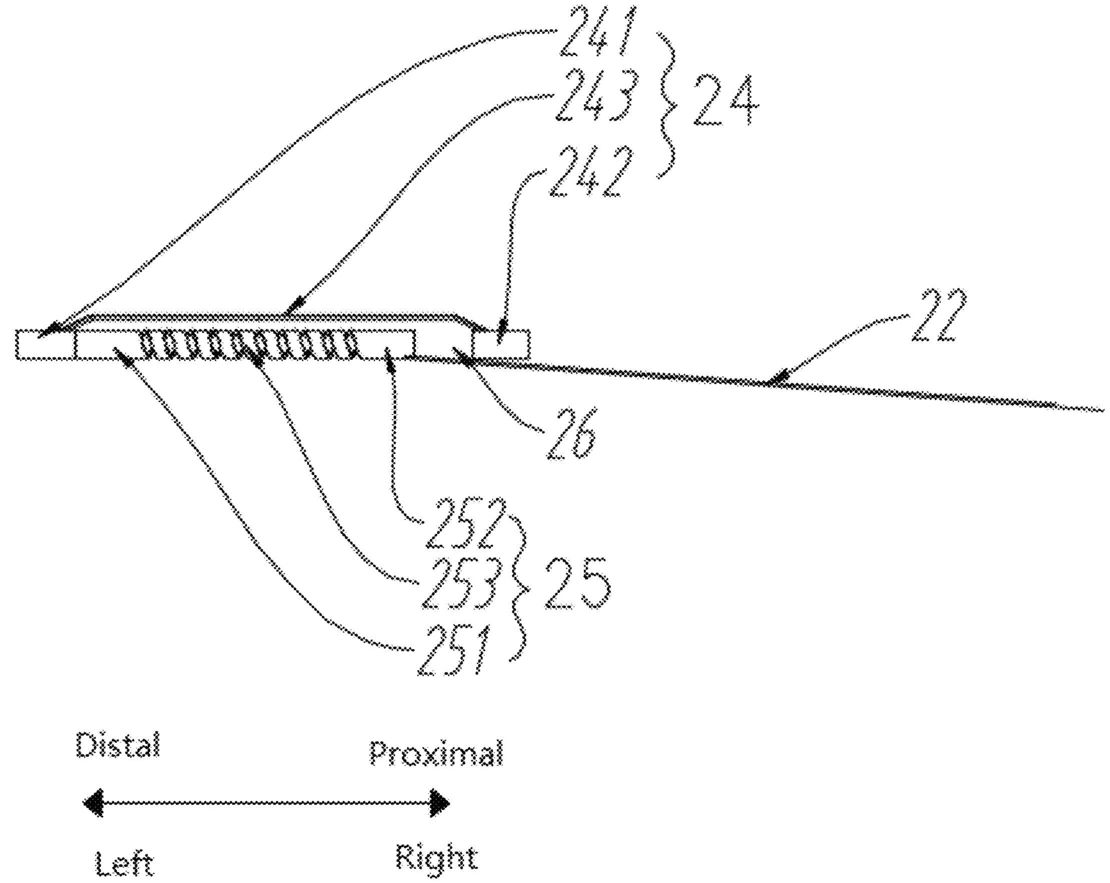
FIG. 4 is a schematic diagram of a structure of an unlocking structure.
Figure 5:
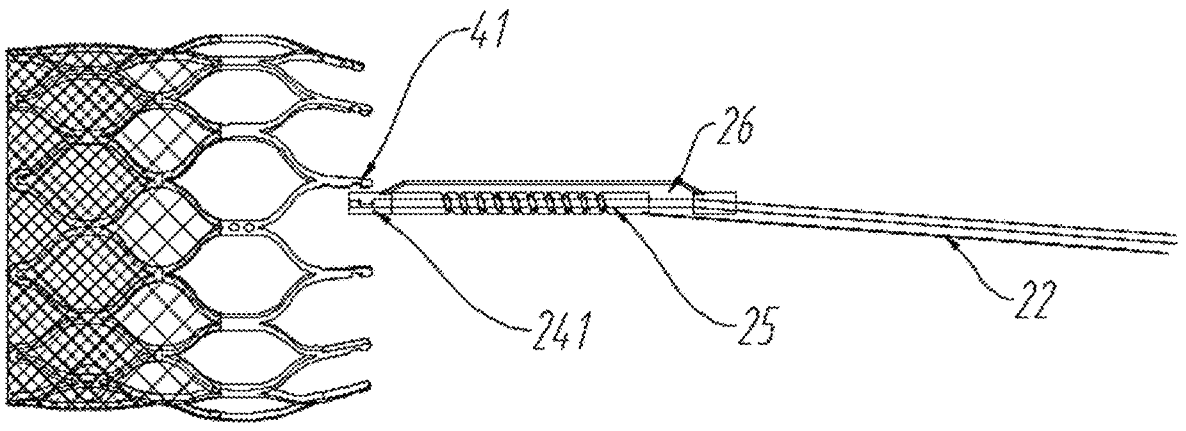
FIG. 5 is a first schematic diagram of cooperation among an unlocking structure, a hanging ear, and a hanging head.
Figure 6:
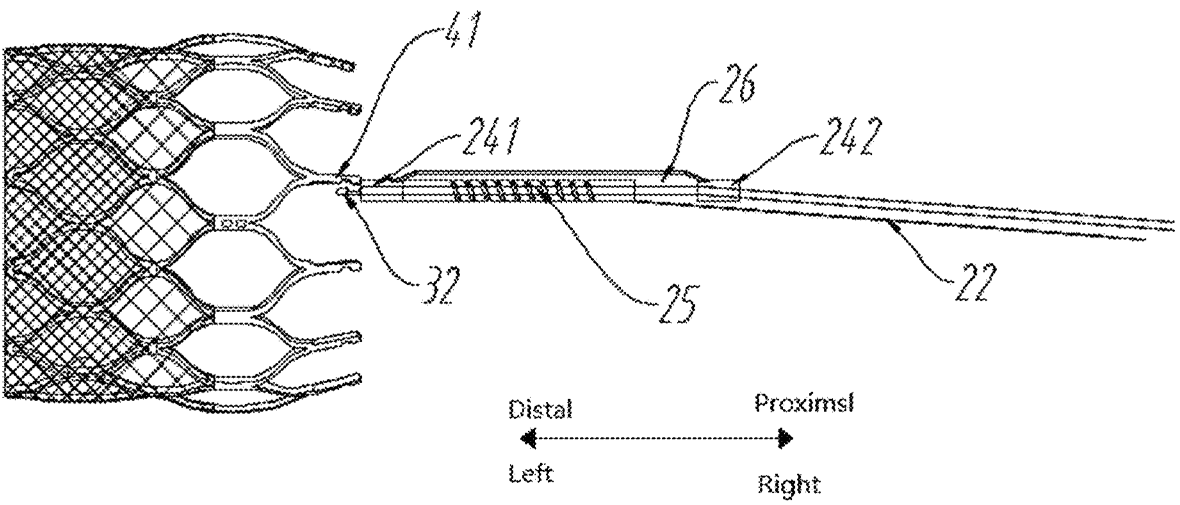
FIG. 6 is a second schematic diagram of cooperation among an unlocking structure, a hanging ear, and a hanging head.
Figure 7:
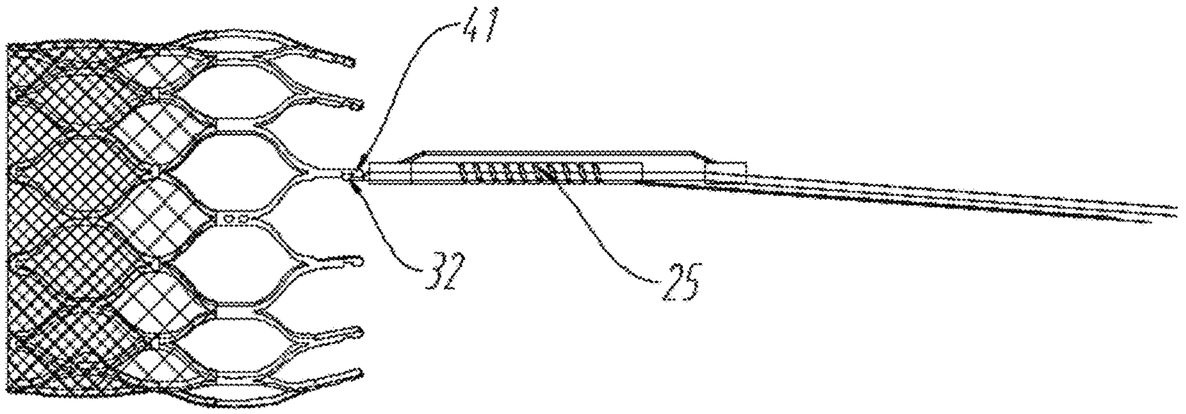
FIG. 7 is a third schematic diagram of cooperation among an unlocking structure, a hanging ear, and a hanging head.

Referring to FIG. 4, for the limiting structure 24, the limiting structure 24 includes the first tube 241, the second tube 242, and the connecting strip 243. The connecting strip 243 has certain rigidity. The first tube 241 and the second tube 242 are connected through the connecting strip 243, and the connecting strip 243 is in a long strip shape, such that relative positions of the first tube 241 and the second tube 242 are kept basically unchanged, and in other words, the length of the interval space is basically unchanged. In a natural state, the length of the spring tube 25 is less than or equal to the length of the interval space, and therefore the spring tube 25 may be arranged in the interval space. One end (a distal end) of the spring tube 25 is connected to the first tube 241, such that relative positions of the distal end of the spring tube 25 and the first tube 241 are fixed, and the other end (a proximal end) of the spring tube 25 is suspended. Since the length of the spring tube 25 is less than or equal to the length of the interval space, the adjustment space 26 is formed between a proximal end of the spring tube 25 and the second tube 242 (when the length of the spring tube 25 is equal to the length of the interval space, the length of the adjustment space 26 is 0). The spring tube 25 has elastic capabilities (similar to a spring), and in an axial direction of the spring tube 25, the spring tube 25 may be compressed or stretched, thereby changing the length of the spring tube 25.

The spring tube 25, the first tube 241, and the second tube 242 are all tubular structures, such that the hanging ear 32 can penetrate through the unlocking tube 23.

The objective of the present disclosure is to solve the problems about the connection between the hanging ears 32 and the hanging heads 41, and normal separation between the hanging ears 32 and the hanging heads 41 during releasing the valve stent 4.

In the present disclosure, the outer tube 21 is a metal tube, and the distal end of the outer tube 21 is connected with the plurality of unlocking structures. For ease of understanding, one of the unlocking structures is used as an example for explanation. The unlocking structure includes the unlocking tube 23 and the traction strip 22. A distal end of the traction strip 22 is connected to the proximal end of the spring tube 25, and a proximal end of the traction strip 22 is connected to the distal end of the outer tube 21. The traction strip 22 is a metal strip and has certain rigidity. In other words, in a normal usage scenario, the traction strip 22 is basically not changed (or a low bending degree), such that relative positions of the distal end of the outer tube 21 and the proximal end of the spring tube 25 are basically kept unchanged.

The inner tube 31 is sleeved with the outer tube 21, a proximal end of the hanging ear 32 is connected to the distal end of the inner tube 31, and the hanging ear 32 is integrally in a long strip shape and may penetrate through the second tube 242 and the spring tube 25, such that a distal end of the hanging ear 32 is located in the first tube 241 (the spring tube 25 is in the natural state).

In the natural state, the distal end of the hanging ear 32 is located inside the first tube 241. When the hanging ear 32 needs to be connected to the hanging head 41 on the valve stent 4, the distal end of the hanging ear 32 needs to be exposed, and in this case, the first tube 241 is manually pressed towards the proximal side. According to an embodiment shown in FIG. 5, the first tube 241 is pushed rightwards to move rightwards, the second tube 242 and the first tube 241 are connected through the connecting strip 243, such that the position of the second tube 242 relative to the first tube 241 is unchanged, and therefore the second tube 242 synchronously moves rightwards. Since a left end (the distal end) of the spring tube 25 is connected to the first tube 241, the left end of the spring tube 25 moves rightwards as well. A right end (the proximal end) of the spring tube 25 is connected to the traction strip 22, the traction strip 22 has certain rigidity, which means that the traction strip 22 hinders the right end of the spring tube 25 from moving rightwards, and as a result, the spring tube 25 is compressed, leading to an increase in the length of the adjustment space 26. Since the first tube 241 moves rightwards and the position of the hanging ear 32 is kept unchanged, the distal end (a left end) of the hanging ear 32 is exposed from the first tube 241 (shown in FIG. 6), thereby facilitating the connection between the distal end of the hanging ear 32 and the hanging head 41.

Figure 8:
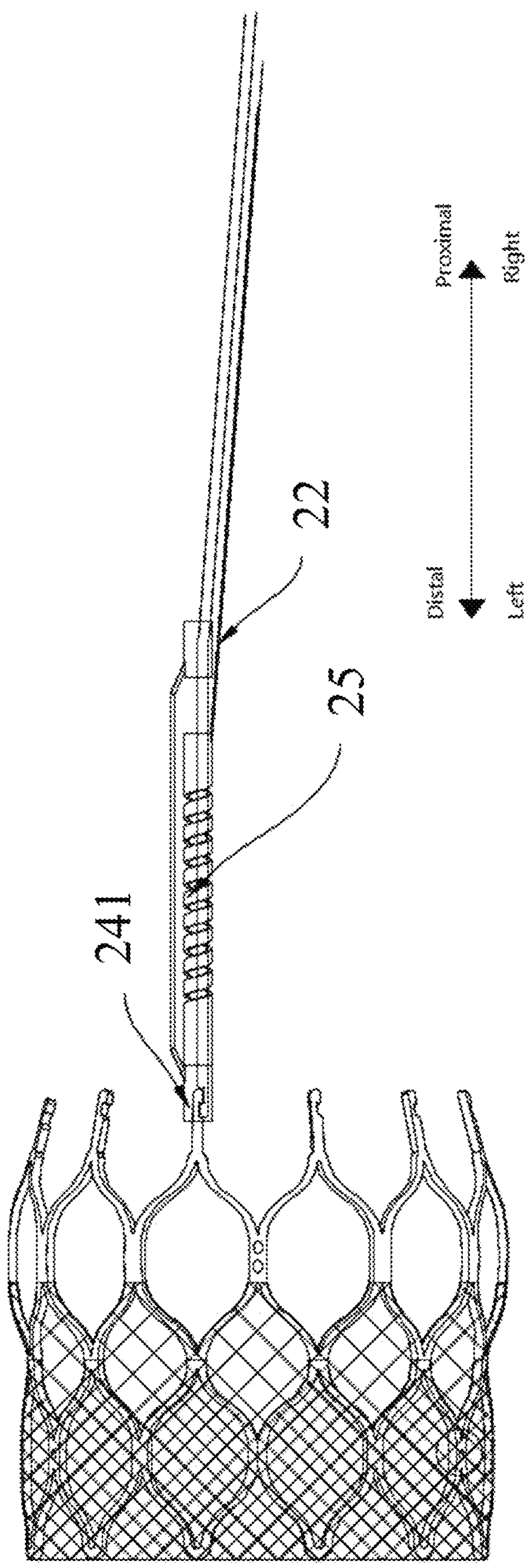
FIG. 8 is a fourth schematic diagram of cooperation among an unlocking structure, a hanging ear, and a hanging head.

After the hanging ear 32 and the hanging head 41 are connected (shown in FIG. 7), the first tube 241 is released. Since the spring tube 25 is compressed, and the position of the right end (the proximal end) of the spring tube 25 is limited by the traction strip 22, the left end (the distal end) of the spring tube 25 moves leftwards, such that the first tube 241 and the second tube 242 synchronously move leftwards, thereby causing the distal end of the hanging ear 32 to re-enter the first tube 241. Due to the connection between the hanging ear 32 and the hanging head 41, the connection position of the hanging ear 32 and the hanging head 41 is located inside the first tube 241 (as shown in FIG. 8), and due to limitation of the first tube 241, the hanging head 41 cannot disengage from the hanging ear 32.

During the interventional surgery, when the valve stent 4 is delivered to the aortic valve, the valve stent 4 needs to be released to replace a failed native valve. When the aortic valve is released, the outer tube 21 is pulled to the proximal side (to right), and the inner tube 31 is kept stationary. Since the outer tube 21 moves rightwards, the traction strip 22 is driven to move rightwards, and the distal end of the traction strip 22 is connected to the proximal end of the spring tube 25, thereby causing the proximal end of the spring tube 25 to move rightwards. In most cases, the spring tube 25 integrally moves rightwards, thereby causing the first tube 241 to move rightwards (i.e., the whole unlocking tube 23 moves rightwards), such that the connection position between the hanging ear 32 and the hanging head 41 is exposed from the first tube 241, and the hanging ear 32 can be released from the hanging head 41 to achieve the purpose of releasing the valve stent 4.

Figure 9:
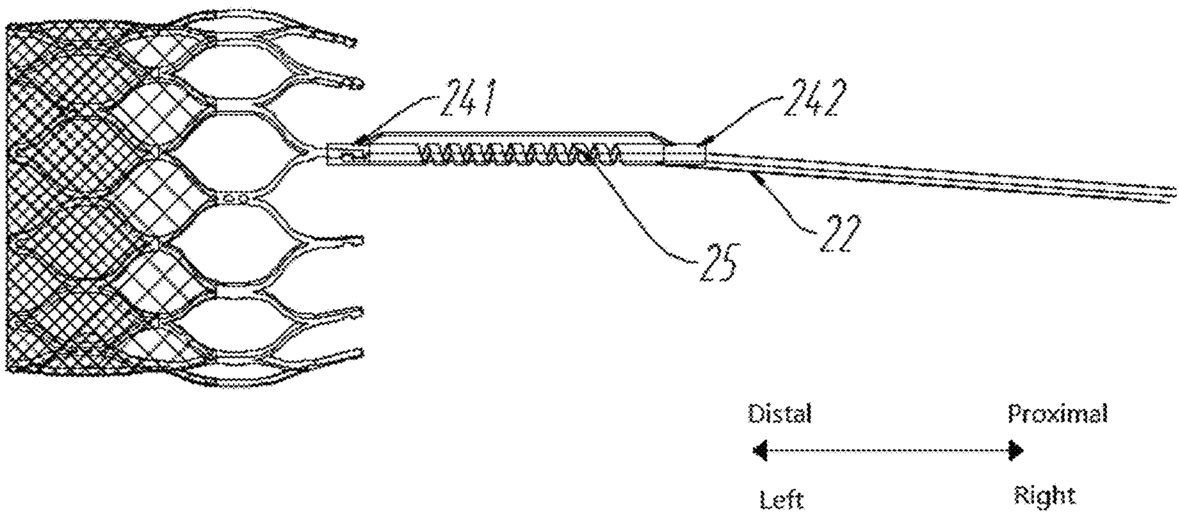
FIG. 9 is a fifth schematic diagram of cooperation among an unlocking structure, a hanging ear, and a hanging head.
Figure 10:
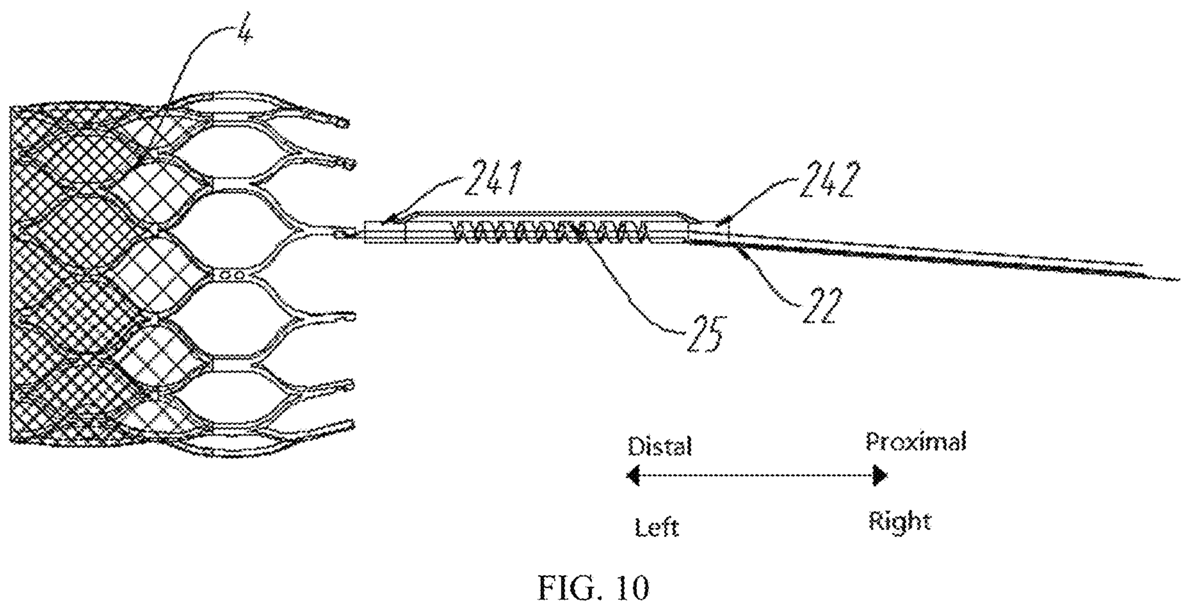
FIG. 10 is a sixth schematic diagram of cooperation among an unlocking structure, a hanging ear, and a hanging head.

In some cases, the spring tube 25 is subjected to certain external resistance, and as a result, the spring tube 25 cannot integrally move towards a right side when the right end of the spring tube 25 is pulled towards the right side. Instead, the phenomenon that the spring tube 25 is stretched occurs, in this case, the position of the left end of the spring tube 25 is still kept unchanged, and therefore the connection position of the hanging ear 32 and the hanging head 41 cannot be exposed from the first tube 241. In this case, the traction strip 22 is pulled towards the right side, the traction strip 22 pulls the right end of the spring tube 25 to move rightwards, the spring tube 25 is stretched, and meanwhile the right end of the spring tube 25 moves towards the second tube 242, thereby shortening the adjustment space 26 until the right end of the spring tube 25 makes contact with the second tube 242 (as shown in FIG. 9). By continuously pulling the traction strip 22 towards the right side, the spring tube 25 may push the second tube 242 to move towards the right side, and the second tube 242 is connected to the first tube 241 through the connecting strip 243, thereby causing the first tube 241 to move towards the right side, so as to ensure that the connection position of the hanging ear 32 and the hanging head 41 can be normally exposed (shown in FIG. 10), the valve stent 4 can be successfully released, and the interventional surgery is normally proceeded.

Additionally, in the natural state, the length of the adjustment space 26 is not greater than 5 mm, such that when the valve stent 4 is released, it is only necessary to ensure additional 5 mm of proximal pull to ensure successful release of the valve stent 4, which is convenient and quick.

Preferably, the length of the adjustment space 26 is 0. Therefore, in the natural state, the other end (the proximal end) of the spring tube abuts against the second tube. Therefore, when the valve stent 4 is released, the traction strip 22 is pulled towards the right side, thereby directly causing the second tube 242 to move rightwards and the first tube 241 to move rightwards as well, so as to ensure that the connection position of the hanging ear 32 and the hanging head 41 can be immediately exposed, and the valve stent 4 can be successfully released.

When the inner tube apparatus is arranged in the outer sheath, the outer sheath may push the spring tube towards the distal side, thereby causing the spring tube to move towards the distal side, ensuring that the connection position of the hanging ear 32 and the hanging head 41 is located inside the first tube 241, and preventing the hanging ear 32 from disengaging from the hanging head 41.

One end of the first tube 241 close to the second tube 242 is provided with a first connection point, and the first connection point is located on a peripheral surface of the first tube 241. One end of the second tube 242 close to the first tube 241 is provided with a second connection point, and the second connection point is located on a peripheral surface of the second tube 242. In a circumferential direction of the first tube 241, the first connection point and the second connection point are located at the same position, one end of the connecting strip 243 is connected to the first connection point, and the other end of the connecting strip is connected to the second connection point.

The connecting strip 243 includes a first inclined segment, a straight segment, and a second inclined segment, which are sequentially connected, and the straight segment is parallel to the axis of the first tube 241.

In a direction from the first tube 241 to the second tube 242, the first inclined segment inclines towards a radial outer side of the first tube 241, and the second inclined segment inclines towards a radial inner side of the first tube 241.

The length of the first inclined segment is equal to the length of the second inclined segment, and the length of the straight segment is far greater than the length of the first inclined segment. An inclination direction of the first inclined segment and the second inclined segment keeps the straight segment away from the spring tube 25, such that in the process of extension and retraction of the spring tube 25, the connecting strip 243 may not be stuck in the spring tube 25, thereby ensuring normal extension and retraction of the spring tube 25 and smooth proceeding of the interventional surgery.

The spring tube 25 includes a first tube segment 251, a spring segment 253, and a second tube segment 252, which are sequentially connected. The first tube segment 251 is connected to the first tube 241, and the traction strip 22 is connected to the second tube segment 252. The first tube segment 251 cannot be compressed or deformed, such that the first tube segment 251 can be conveniently connected to the first tube 241 (welding may be adopted), thereby causing the first tube 241 to be connected to the spring tube 25. The arrangement of the second tube segment 252 allows for convenient connection with the traction strip 22, such that the traction strip 22 can be connected to the spring tube 25. The arrangement of the spring segment 253 allows for extension and retraction of the spring tube 25.

An internal diameter of the first tube 241, an internal diameter of the first tube segment 251, an internal diameter of the second tube segment 252, and an internal diameter of the second tube 242 are equal, and an external diameter of the first tube 241, an external diameter of the first tube segment 251, an external diameter of the second tube segment 252, and an external diameter of the second tube 242 are equal.

In the natural state, an internal diameter of the spring segment is equal to the internal diameter of the first tube segment, and an external diameter of the spring segment is equal to the external diameter of the first tube segment.

Internal diameters and external diameters of various positions of the unlocking tube 23 (excluding the connecting strip 243) are basically consistent, thereby facilitating the insertion of the hanging ear 32 into the unlocking tube 23.

The present disclosure further relates to an unlocking tube 23. The unlocking tube 23 has been described in detail previously and is not repeated herein.

It should be understood that the above implementations are merely exemplary and not restrictive. Without departing from the fundamental principles of the present disclosure, those skilled in the art may make various obvious or equivalent modifications or substitutions to the above details, all of which will be included within the scope of the claims of the present disclosure.

What is claimed is:

1. An unlocking tube as part of a heart valve delivery assembly, wherein:

the unlocking tube comprises a spring tube and a limiting structure, the limiting structure comprises a first tube, a second tube and a connecting strip, wherein the first tube and the second tube are coaxially arranged and axially spaced from each other creating an interval space therebetween, the first tube and the second tube are connected through the connecting strip, the spring tube is located in the interval space with one end connected to the first tube, an axis of the spring tube and an axis of the first tube are located on the same straight line, an adjustment space is formed between the other end of the spring tube and the second tube.

2. A heart valve delivery assembly, comprising an outer sheath, an outer tube apparatus, an inner tube apparatus, and a valve stent, wherein:

the outer tube apparatus comprises an outer tube and a plurality of unlocking structures; each unlocking structure comprises an unlocking tube and a traction strip which are interconnected, within each unlocking structure:

the unlocking tube comprises a spring tube and a limiting structure, the limiting structure comprises a first tube, a second tube, and a connecting strip, wherein the first tube and the second tube are coaxially arranged and axially spaced from each other creating an interval space therebetween, the first tube and the second tube are connected through the connecting strip, the spring tube is located in the interval space with one end connected to the first tube, an axis of the spring tube and an axis of the first tube are located on the same straight line, an adjustment space is formed between the other end of the spring tube and the second tube, the traction strip is connected to the other end of the spring tube, and the unlocking structure is connected to a distal end of the outer tube through the traction strip; and in a circumferential direction of the outer tube, the plurality of unlocking structures are arranged with equal angles;

the inner tube apparatus comprises an inner tube and a plurality of hanging ears, the number of the hanging ears is equal to the number of the unlocking structures, and each hanging ear corresponds to a respective unlocking structure, the plurality of hanging ears are connected to a distal end of the inner tube, in a circumferential direction of the inner tube the plurality of hanging ears are arranged with equal angles, the inner tube is located inside the outer tube, and each hanging ear extends through a second tube, spring tube, and first tube of a respective unlocking structure of the outer tube apparatus;

the valve stent comprises a stent with a valve therein, one end of the stent comprising a plurality of hanging heads, the number of the hanging heads is equal to the number of the hanging ears, and each hanging head corresponds to a respective hanging ear, and each hanging head is connected to a respective hanging ear of the inner tube apparatus; and the outer tube is sleeved with the outer sheath.

3. The heart valve delivery assembly according to claim 2, wherein within each unlocking structure:

one end of the first tube close to the second tube is provided with a first connection point, which is located on a peripheral surface of the first tube, one end of the second tube close to the first tube is provided with a second connection point, which is located on a peripheral surface of the second tube, in a circumferential direction of the first tube, the first connection point and the second connection point are located at the same position, one end of the connecting strip is connected to the first connection point, and the other end of the connecting strip is connected to the second connection point;

the connecting strip comprises a first inclined segment, a straight segment, and a second inclined segment, which are sequentially connected, and the straight segment is parallel to the axis of the first tube; and in a direction from the first tube to the second tube, the first inclined segment inclines towards a radial outer side of the first tube, and the second inclined segment inclines towards a radial inner side of the first tube.

4. The heart valve delivery assembly according to claim 2, wherein within each unlocking structure:

the spring tube comprises a first tube segment, a spring segment, and a second tube segment, which are sequentially connected, the first tube segment is connected to the first tube, and the traction strip is connected to the second tube segment.

5. The heart valve delivery assembly according to claim 4, wherein within each unlocking structure:

an internal diameter of the first tube, an internal diameter of the first tube segment, an internal diameter of the second tube segment, and an internal diameter of the second tube are equal, and an external diameter of the first tube, an external diameter of the first tube segment, an external diameter of the second tube segment, and an external diameter of the second tube are equal; and in a natural state, an internal diameter of the spring segment is equal to the internal diameter of the first tube segment and an external diameter of the spring segment is equal to the external diameter of the first tube segment.

* * * * *